US00PP31091P2

(12) United States Plant Patent
Van Swieten

(10) Patent No.: US PP31,091 P2
(45) Date of Patent: Nov. 19, 2019

(54) ***PHALAENOPSIS* ORCHID PLANT NAMED 'PHALGORFON'**

(50) Latin Name: ***Phalaenopsis* hybrid**
Varietal Denomination: PHALGORFON

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,280

(22) Filed: Oct. 25, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

(56) References Cited

PUBLICATIONS

GTITM UPOVROM Citation for 'Phalgorfon' as per QZ PBR 20171088; Jun. 16, 2017; 1 page.*
EU Community Plant Variety Rights Application No. 2017/1088, Application n°A201701214, filed Apr. 24, 2017, 8 pages.
EU Community Plant Variety Office Official Gazette, Mar. 2017, Jun. 15, 2017, cover page and pp. 36, 57.
EU Community Plant Variety Office Official Gazette, Feb. 2018, Apr. 15, 2018, cover page and p. 72.
EU Community Plant Variety Rights Application No. 2018/1191, Application n°A201801160, filed Apr. 26, 2018, 8 pages.
EU Community Plant Variety Office Official Gazette, Apr. 2018, Aug. 15, 2018, cover page and pp. 37, 54.

* cited by examiner

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALGORFON', particularly characterized by having white, flecked flowers with red-purple lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGORFON'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGORFON'.

The new *Phalaenopsis* plant is a product of a planned breeding program conducted by the inventor in Bleiswijk, The Netherlands. The objective of this breeding program was to create a new *Phalaenopsis* plant with numerous attractive white, flecked flowers with red-purple lips, suitable for potted plant production.

The new *Phalaenopsis* plant 'PHALGORFON' is a result of cross-pollination made by the inventor in January 2010 in Bleiswijk, The Netherlands of the proprietary female, or seed parent, *Phalaenopsis* hybrid '22791-01' (unpatented) with the proprietary male, or pollen parent, *Phalaenopsis* hybrid '01-3136' (unpatented).

The new *Phalaenopsis* was selected by the inventor as a single plant within the progeny of the stated cross-pollination in a controlled greenhouse in Bleiswijk, The Netherlands in November 2012. Asexual reproduction of the new *Phalaenopsis* plant by meristem tissue culture since 2015 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017, and Apr. 26, 2018. 'PHALGORFON' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALGORFON' as a new and distinct variety of *Phalaenopsis* plant.

1) White, flecked flowers with red-purple lips (intensity and number of flecks depend on the temperature during the growing period);
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in August 2018. Colors in the photographs may differ from the color values cited in the detailed botanical description, which accurately describe the actual colors of the new variety.

DESCRIPTION OF THE NEW VARIETY

Figure 1:
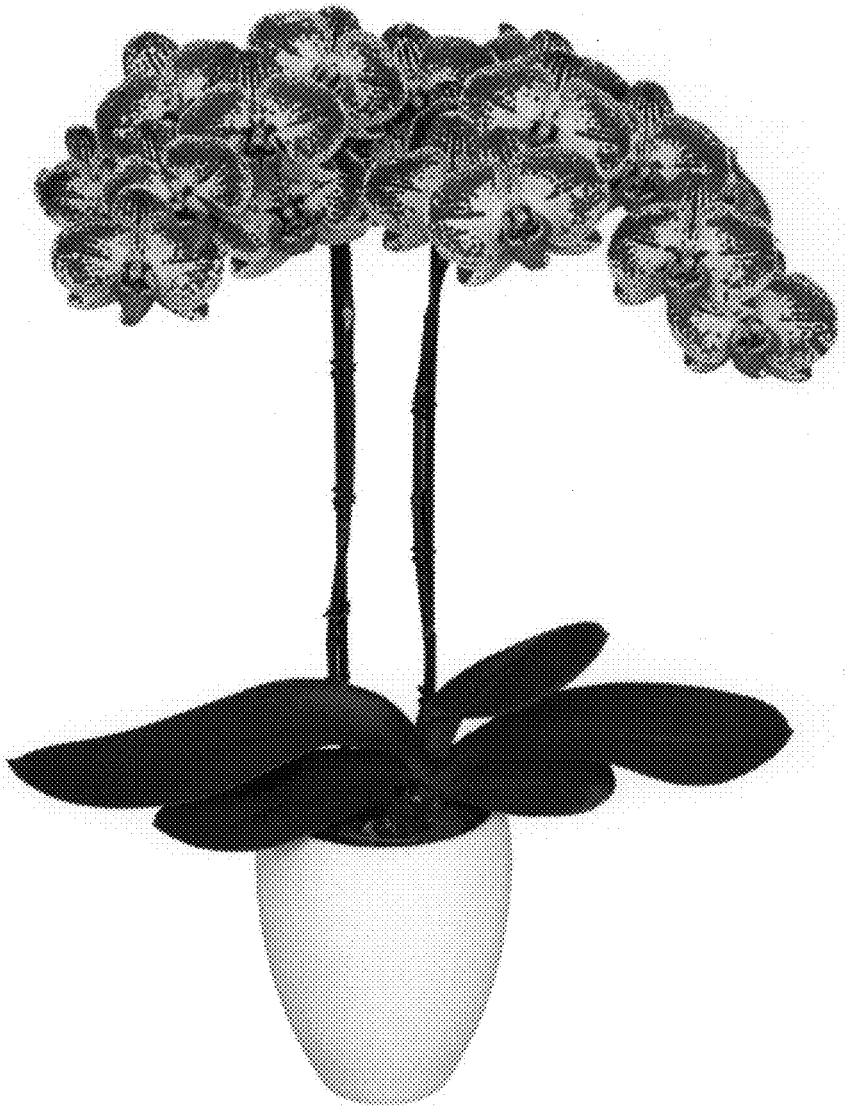
FIG. 1 shows the overall plant habit, including blooms and foliage of 'PHALGORFON'.
Figure 2:
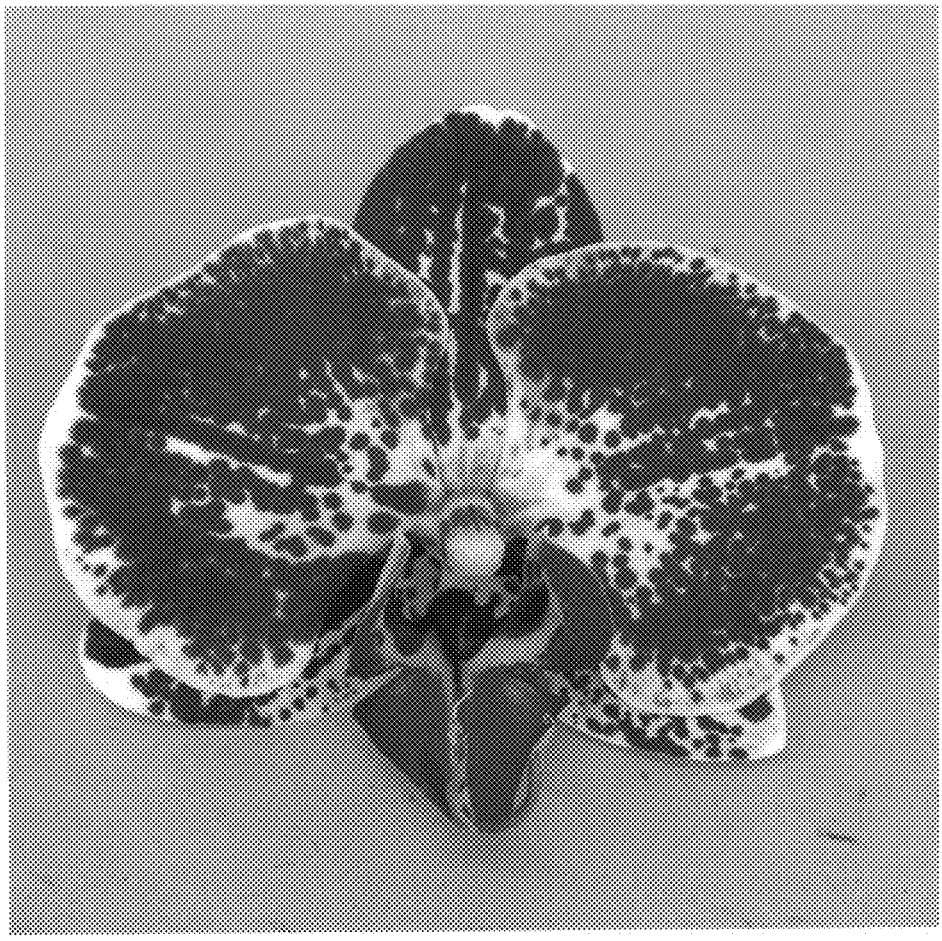
FIG. 2 shows a close-up of a flower of 'PHALGORFON'.
Figure 3:
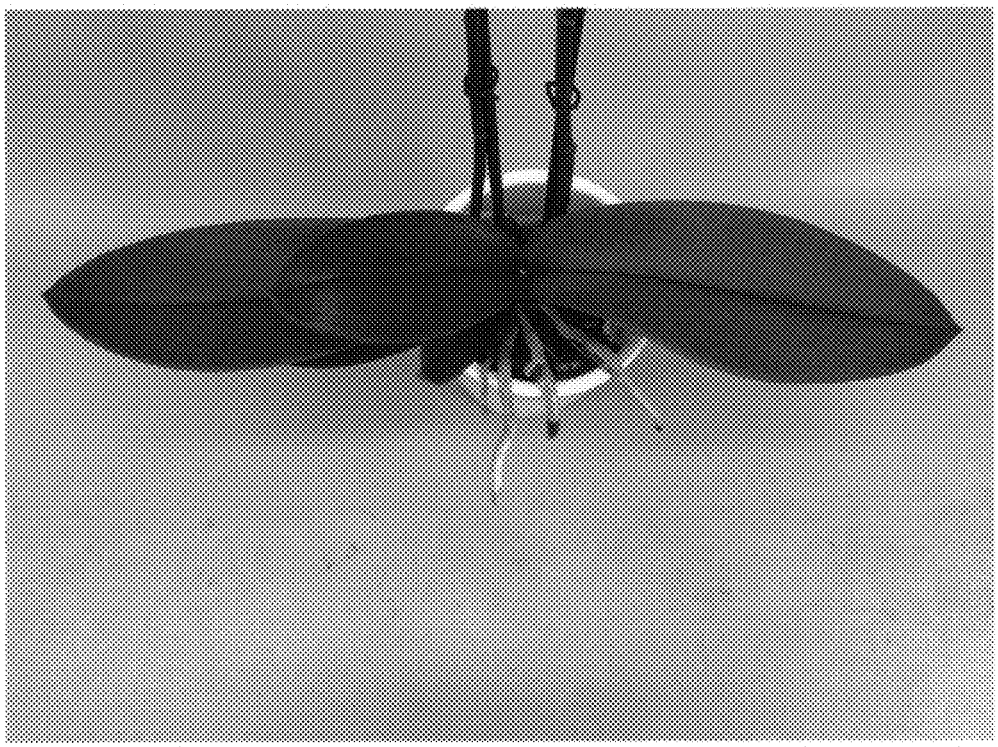
FIG. 3 shows an overhead view of the leaves of 'PHALGORFON'.

The following detailed description sets forth the distinctive characteristics of 'PHALGORFON'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in August 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGORFON'.

Parentage:

*Female parent*.—*Phalaenopsis* cultivar '22791-01' (unpatented).

*Male parent*.—*Phalaenopsis* cultivar '01-3136' (unpatented).

Propagation:

*Type*.—Meristem tissue culture.

Roots:

*Root description*.—Greyed-green colored roots (between RHS 190B and 190C) with branching lateral roots having dark red colored root tips (RHS 187A).

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme to panicle inflorescence.

*Height (from soil level to top of inflorescence)*.—Approximately 47.0 cm to 52.0 cm.

*Width (measured from leaf tips)*.—About 43.0 cm to 45.0 cm.

*Vigor*.—Moderate.

Leaves:

*Mature leaves*.—Quantity per plant: 7 to 9 leaves are produced before flowering. Length (fully expanded): 21.0 cm to 23.0 cm. Width: 8.0 cm to 9.0 cm. Shape: Oblong. Base shape: Moderately elongated. Apex: Obtuse unequal. Leaf blade angle with the petiole (measured from the horizontal position): Between 10 degrees and 25 degrees. Leaf margin: Entire. Color: Upper surface: RHS 146A. Lower surface: RHS 146B with diluting dark red region (RHS 187A) toward the tip and margin. Texture (upper surface): Rough. Thickness: 2.5 mm to 2.7 mm. Venation: Pattern: Parallel. Color of the midvein: Upper surface: RHS 147A and slightly RHS 187A. Lower surface: RHS 147B and diluting RHS 187A.

Peduncle:

*Quantity per plant*.—1 to 3.

*Number of flowers per peduncle*.—12 to 22.

*Length*.—47.0 cm to 52.0 cm.

*Diameter*.—6.1 mm to 6.6 mm.

*Strength*.—Strong.

*Aspect*.—Upright to slightly pendant.

*Texture*.—Smooth.

*Color*.—Brown (RHS 200A).

*Internode length*.—3.5 cm to 4.5 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 200.0 mm to 230.0 mm.

*Flowering time*.—First flowers can be expected 10 to 11 months after planting in a 12 cm (diameter) pot.

*Flower*.—Height: 70.0 mm to 75.0 mm. Diameter: 85.0 mm to 90.0 mm. Depth of lip: 21.0 mm to 23.0 mm.

*Flower longevity*.—On the plant: 8 to 13 weeks.

*Fragrance*.—Absent.

*Flower bud*.—Average size: Large. Length: 21.0 mm to 23.0 mm. Width: 18.0 mm to 20.0 mm. Shape: Egg shaped. Color: Green (RHS 146D) with a touch of diluting dark purplish-red (RHS N79B).

*Petals*.—Arrangement: Open/free. Shape: Semi-circular. Apex: Rounded asymmetric. Margin: Slightly undulated. Length (from base to tip): 39.0 mm to 41.0 mm. Width: 49.0 mm to 51.0 mm. Color (when fully opened): Upper surface: Basic color: White (RHS NN155C). Over color: Dark purplish-red (RHS N79B to N79C). Lower surface: Basic color: Very light purple (RHS 76C). Over color: White edge (RHS NN155C) and diluting dark purplish-red flecks (RHS N79C).

*Dorsal sepal*.—Shape: Elliptic. Apex: Obtuse symmetric. Margin: Entire. Length (from base to tip): 42.0 mm to 44.0 mm. Width: 30.0 mm to 32.0 mm. Color (when fully opened): Upper surface: Basic color: White (RHS NN155C). Over color: Dark purplish-red flecks (RHS N79B to N79C). Lower surface: Basic color: Light purple (RHS 76A). Over color: Light yellow-green (RHS 145D) and slightly dark purplish-red edge (RHS N79C).

*Lateral sepals*.—Shape: Ovate. Apex: Obtuse asymmetric. Margin: Entire. Length (from base to tip): 41.0 mm to 43.0 mm. Width: 27.0 mm to 29.0 mm. Color (when fully opened): Upper surface: Basic color: White (RHS NN155C). Over color: Light yellow-green (RHS 145D) at the base; dark purplish-red flecks (RHS N79B to N79C). Lower surface: Basic color: Light purple (RHS 76A). Over color: Yellow-green (RHS 146D) at the base; dark purplish vein and diluting flecks (RHS N79B) toward one margin and reddish-purple region (RHS N78B) toward the tip.

*Labellum* (*lip*).—Whiskers: Present. Length of whiskers: 11.0 mm to 13.0 mm. Color of whiskers: Dark red (RHS 59A) with white tip (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 19.0 mm to 21.0 mm. Width: 12.0 mm to 14.0 mm. Color: White (RHS NN155C) at the base with dark red stripes (RHS 59A); slightly yellow toward the callus (RHS 12B); dark red (RHS 59A) on one side and red-purple toward other side (RHS N78A).

*Apical lobe*.—Shape: Triangular. Margin: Entire. Length: 21.0 mm to 23.0 mm. Width: 21.0 mm to 23.0 mm. Color: Slightly light yellow (RHS 12C) at the base with a dark red (RHS 59A) stripe in the middle; dark red wings (RHS 183B) and red-purple (mix of RHS N78A and NN78A) toward the whiskers.

*Callus*.—Average size: Medium. Height: 6.0 mm to 7.0 mm. Length: 6.0 mm to 7.0 mm. Width: 3.0 mm to 4.0 mm. Color: Dark red (RHS 187A) and light greenish-yellow (RHS 8C) in the middle.

Reproductive organs:

*Column*.—Length: 9.0 mm to 11.0 mm. Diameter: 5.5 mm to 5.8 mm. Color: Reddish-purple (RHS N78A) at the base and light reddish-purple (RHS N78D) toward the tip.

*Pollinia*.—Quantity: 2. Diameter: 0.8 mm to 1.0 mm. Color: Orange (RHS 24A).

*Ovary*.—Length: 10.0 mm to 12.0 mm. Diameter: 2.3 mm to 2.6 mm. Color: Yellow-green (RHS 146D) and light purple (RHS 76A) toward the flower.

*Pedicel*.—Length: 36.0 mm to 38.0 mm. Diameter: 2.6 mm to 3.3 mm. Color: Green (RHS 146C) at the base and yellow-green (RHS 146D) and light purple (RHS 76A) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGORFON' differs from female parent plant '22791-01' (unpatented) in that 'PHALGORFON' has calluses that are dark red and light greenish-yellow in the middle, and flowers with a main color of white with a flecked pattern, whereas '22791-01' has calluses that are yellow and dotted, and flowers with a main color of purple with a center pattern. Additionally, 'PHALGORFON' has smaller flowers than '22791-01'.

The male parent plant of 'PHALGORFON', cultivar '01-3136', is no longer in existence, so a meaningful comparison cannot be made.

'PHALGORFON' is most similar to the commercial *Phalaenopsis* plants named 'PHALFONXHE' (U.S. Plant Pat. No. 29,451) and 'PHALFEQBIN' (U.S. Plant Pat. No. 29,615). 'PHALGORFON' differs from the commercial variety 'PHALFONXHE' in that 'PHALGORFON' has whiskers that are dark red with white tips, whereas 'PHALFONXHE' has whiskers that are purple with a white edge. Additionally, 'PHALGORFON' has larger flowers and wider leaves than 'PHALFONXHE'.

'PHALGORFON' differs from the commercial variety 'PHALFEQBIN' in that 'PHALGORFON' has whiskers that are dark red with white tips and rounded asymmetric petal apexes, whereas 'PHALFEQBIN' has whiskers that are purple with white spots and obtuse asymmetric petal apexes. Additionally, 'PHALGORFON' has larger flowers and wider leaves than 'PHALFEQBIN'.

I claim:

1. A new and distinct variety of *Phalaenopsis* plant named 'PHALGORFON', substantially as described and illustrated herein.

* * * * *